(12) United States Patent
Booher, Sr.

(10) Patent No.: US 8,550,088 B1
(45) Date of Patent: Oct. 8, 2013

(54) CERVICAL STABILIZATION DEVICE

(75) Inventor: Benjamin V. Booher, Sr., Scottsdale, AZ (US)

(73) Assignee: TechDyne LLC, Scottsdale, AZ (US)

( * ) Notice: Subject to any disclaimer, the term of this patent is extended or adjusted under 35 U.S.C. 154(b) by 932 days.

(21) Appl. No.: 12/537,700

(22) Filed: Aug. 7, 2009

Related U.S. Application Data

(60) Provisional application No. 61/089,428, filed on Aug. 15, 2008, provisional application No. 61/164,815, filed on Mar. 30, 2009.

(51) Int. Cl.
*A61F 13/00* (2006.01)

(52) U.S. Cl.
USPC .............................................. 128/846; 600/37

(58) Field of Classification Search
USPC ............ 128/897, DIG. 25; 600/29–35, 37–41
See application file for complete search history.

(56) References Cited

U.S. PATENT DOCUMENTS

| | | | |
|---|---|---|---|
| 2,638,093 A * | 5/1953 | Kulick | ............................ 600/29 |
| 2,836,177 A | 5/1958 | Sells | |
| 3,741,216 A | 6/1973 | Yosowitz et al. | |
| 4,128,100 A | 12/1978 | Wendorff | |
| 4,311,543 A | 1/1982 | Strickman et al. | |
| 5,167,237 A | 12/1992 | Rabin et al. | |
| 5,209,754 A | 5/1993 | Ahluwalia | |
| 5,851,188 A | 12/1998 | Bullard et al. | |
| 6,113,580 A | 9/2000 | Dolisi | |
| 6,526,980 B1 | 3/2003 | Tracy et al. | |
| 6,923,185 B1 | 8/2005 | Koch | |
| 6,994,678 B2 | 2/2006 | Baxter-Jones et al. | |
| 7,153,280 B2 | 12/2006 | Welch | |
| 2005/0277948 A1 | 12/2005 | Cedars et al. | |
| 2007/0225744 A1 | 9/2007 | Nobles et al. | |
| 2008/0154284 A1 | 6/2008 | Varma | |
| 2008/0269773 A1 | 10/2008 | George | |

FOREIGN PATENT DOCUMENTS

| | | |
|---|---|---|
| KR | 10-2001-0110556 | 12/2001 |
| KR | 20010110556 | 12/2001 |

\* cited by examiner

*Primary Examiner* — Patricia Bianco
*Assistant Examiner* — Camtu Nguyen
(74) *Attorney, Agent, or Firm* — Booth Udall Fuller, PLC

(57) ABSTRACT

A system and method for stabilizing an incontinent cervix during pregnancy are described. A system may include a nesting portion designed to surround the cervix without applying pressure to the cervix, while supporting the uterus in opposition to the weight of the developing fetus to prevent untimely effacement and dilatation of the cervix; thereby reducing the risk of premature birth and its consequence.

21 Claims, 7 Drawing Sheets

CERVICAL STABILIZATION DEVICE

CROSS REFERENCE TO RELATED APPLICATIONS

This application claims priority to the following U.S. Provisional Patent Applications: 61/089,428, filed Aug. 15, 2008, and 61/164,815, filed Mar. 30, 2009, the disclosures of each of which are hereby incorporated by reference in their entirety.

BACKGROUND

1. Technical Field

This disclosure relates to implementations of a device, with at least some portion thereof designed to be inserted into the vagina, for the purpose of stabilizing the cervix and uterus during pregnancy. Particular implementations may reduce the risk of miscarriage, premature delivery, or stillbirth, resulting from compromise of the organs and structures of the female reproductive system.

2. Background Art

A medical condition commonly known as an "incontinent cervix" (also known as an "insufficient cervix", "incompetent cervix" and "loose cervix") can have serious effects on a pregnant woman and is known to be responsible for the loss of millions of preterm infants each year. Moreover, infants surviving preterm birth often suffer crippling lifelong diseases including autism and cerebral palsy (conditions known to result from premature birth). During a pregnancy, the fetus grows in the uterus, often referred to as the womb. As the fetus grows heavier, the weight bearing down upon the uterus strains upon the cervix. A patient with an incontinent cervix has a weakened cervix that may not be able to handle the added pressure on the cervix resulting from pregnancy. A common treatment for the incontinent cervix is to suture the cervix closed to prevent the cervix from opening further, in a procedure called a cerclage.

Such a condition, with or without cerclage, often requires that the patient be subject to bed rest for an extended period of time. Moreover, cerclage is known to further compromise the cervix which can make future pregnancies even more difficult, and the procedure is also often associated with an instantaneous premature birth event. Therefore, it is desirable to have a non-invasive, non-surgical method of treatment for incontinent cervix in order to retain the fetus in the womb until a viable birth is possible.

SUMMARY

Aspects of this disclosure relate to methods and structure for stabilizing a cervix during pregnancy. In one aspect, a device for stabilizing a cervix of a uterus during pregnancy may comprise a uterine support shoulder comprising an upper shoulder portion configured to contact a portion of a vaginal wall of a vagina proximate entry of the cervix of the uterus into the vagina, the uterus carrying a fetus, the uterine support shoulder coupled to and at least partially circumscribing a nesting area configured to receive a cervix extending from the uterus. The nesting area may comprise a void larger than an outer dimension of the cervix so that the nesting area surrounds but does not engage the cervix. The nesting area may further comprise a vent extending through the nesting area. At least one seat portion may extend anatomically outward and downward from the uterine support shoulder, the at least one seat portion configured to engage walls of the vagina surrounding the cervix and resist movement of the uterine support shoulder away from the portion of the vaginal wall proximate the entry of the cervix of the uterus into the vagina.

Particular implementations of a device for stabilizing a cervix may comprise one or more of the following: The at least one seat portion may comprise a plurality of separate seat portions, each extending in a different radial direction from the uterine support shoulder and each comprising the plurality of ridges. The at least one seat portion may be in communication with an inflatable bladder portion, wherein inflating the bladder portion causes the at least one seat portion to expand and press the at least one seat portion against the vaginal wall. At least one inflatable bladder may be positioned around at least a portion of the nesting area and between the nesting area and the at least one seat portion, wherein inflating the bladder portion causes the at least one seat portion to extend away from the nesting area and press the at least one seat portion against the vaginal wall. At least one inflatable bladder may be positioned around at least a portion of the nesting area, wherein the inflatable bladder portion is configured such that inflating the bladder portion causes the at least one inflatable bladder portion to extend and engage the vaginal wall proximate a lower pelvic structure adjacent the vagina. At least one vent tube may be coupled to the nesting area at the at least one vent in communication with the concave void. At least one inflatable bladder portion may comprise at least two bladder portions adjacent to each other, each of a first and a second of the at least two bladder portions extending from the nesting area along a vent tube coupled to the vent of the nesting area. The at least one inflatable bladder may extend from the nesting area along a vent tube coupled to the vent of the nesting area and the device may further comprise at least another inflatable bladder that extends from the first inflatable bladder along the vent tube away from the first inflatable bladder.

In another aspect, a device for stabilizing a cervix of a uterus of a woman during pregnancy may comprise a uterine support shoulder comprising an upper shoulder configured to contact a portion of a vaginal wall of a vagina proximate entry of the cervix of the uterus into the vagina, the uterus carrying a fetus. The uterine support shoulder may be coupled to and at least partially circumscribe a nesting area configured to receive a cervix extending from the uterus. The nesting area may comprise a void larger than an outer dimension of the cervix so that the nesting area surrounds but does not engage the cervix. The nesting area may further comprise a vent extending through the nesting area. A support may be coupled to the uterine support shoulder and extend away from the uterine support shoulder toward an opening to the vagina; the support may comprise a vent opening coupled to the vent of the nesting area. An external retaining portion may be coupled to the support and configured to couple to the woman outside the vagina to resist movement of the uterine support shoulder away from the portion of the vaginal wall proximate the entry of the cervix of the uterus into the vagina.

Particular implementations of a device for stabilizing a uterus may comprise one or more of the following: The external retaining portion may further comprise a vent coupled to the vent of the support, the external retaining portion vent in communication with the vent of the nesting area and outside the vagina. The external retaining portion may be configured to couple to the woman outside the vagina through at least one of a belt and a garment positioned around the woman.

In yet another aspect, a method of stabilizing a cervix during pregnancy may comprise at least partially surrounding a cervix of a uterus carrying a fetus with a nesting area of a cervical stabilization device without engaging the cervix, permitting the cervix to drain fluid from the nesting area through a vent in the nesting area, supporting a portion of a vaginal wall of a vagina proximate entry of the cervix of the uterus into the vagina with a uterine support shoulder of the cervical stabilization device, the uterine support shoulder at least partially surrounding the nesting area, and maintaining the support of the portion of the vaginal wall proximate entry of the cervix into the vagina through engaging vaginal walls surrounding the cervix with at least one seat portion coupled to and extending anatomically outward and downward from the uterine support shoulder.

Particular implementations of a method of stabilizing a cervix during pregnancy may further comprise one or more of the following: Inserting the cervical stabilization device into the vagina prior to supporting a portion of the vaginal wall proximate the entry of the cervix of the uterus into the vagina and permitting the cervix to further drain the fluid through a vent tube coupled to the vent in the nesting area. Maintaining the support of the portion of the vaginal wall proximate entry of the cervix through engaging vaginal walls surrounding the cervix may comprise engaging the vaginal walls for an extended period of time without removing the cervical stabilization device. Maintaining the support of the portion of the vaginal wall proximate the entry of the cervix of the uterus into the vagina for an extended period of time may comprise maintaining the support at least a week and the maintaining the support at least a week may comprise maintaining the support for at least a month without removing the cervical stabilization device. Particular implementations may further comprise inflating at least one bladder portion positioned beneath the at least one seat portion such that when the at least one bladder is inflated it enlarges and pushes the at least one seat portion toward the vaginal walls surrounding the cervix. Particular implementations may further comprise inflating the at least one bladder portion such that an anatomically lower portion of the at least one bladder portion contacts anatomically lower vaginal tissues proximate an anatomically lower pelvic structure adjacent the vagina. The method may further comprise inflating at least a second bladder adjacent to the at least one bladder, the at least a second bladder positioned beneath the at least one seat portion on a second side of the nesting area. The method may further comprise inflating at least a second bladder adjacent to the at least one bladder, the at least a second bladder being positioned along a vent tube coupled to the vent in the nesting area.

Maintaining the support of the portion of the vaginal wall proximate the entry of the cervix through engaging vaginal walls surrounding the cervix may comprise engaging the vaginal walls with a plurality of separately moveable seat portions each extending in a different radial direction from the uterine support and each contacting a different portion of the vaginal walls surrounding the cervix. Maintaining the support of the portion of the vaginal wall proximate the entry of the cervix of the uterus into the vagina may comprise inflating at least one bladder portion incorporated within the at least one seat portion.

The foregoing and other aspects, features, and advantages will be apparent to those having ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DETAILED DESCRIPTION

Figure 1:
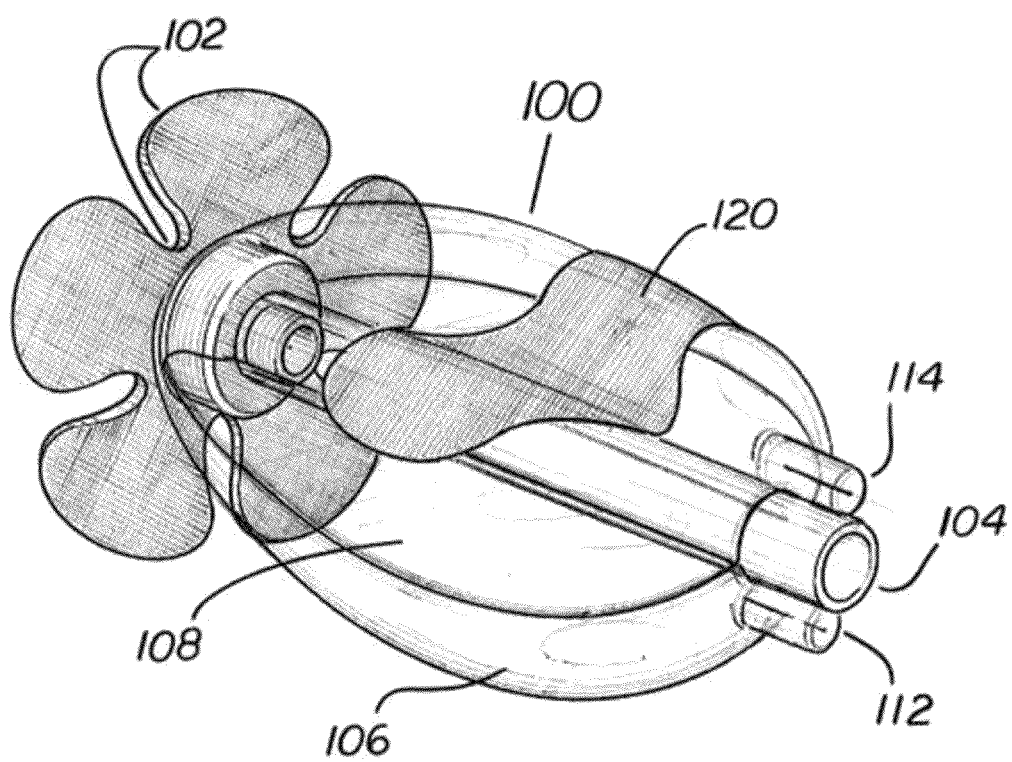
FIG. 1 is an isometric diagram illustrating one particular embodiment of a cervical stabilization device fully inflated and outside the vagina confines.

The following descriptions are of exemplary embodiments of particular implementations of cervical stabilization devices and are not intended to limit the scope, applicability or configuration of the claims in any way. Rather, the following descriptions are intended to provide convenient illustrations for implementing various embodiments of cervical stabilization devices. As will become apparent, changes may be made in the function and/or arrangement of any of the elements described in the disclosed exemplary embodiments without departing from the spirit and scope of the claims.

Embodiments provide for a device that is used to stabilize the cervix, relieving some of the weight bearing down upon the uterus so as to reduce unnecessary strain on or stimulation of the cervix. Conventional devices, used as contraceptives or to retain prolapsed organs (such as the balder, bowel, and uterus) and which are not used or intended for use during pregnancy or to prevent premature births, and those used to clamp the cervix without supporting the uterus, force contact on the cervix by primitive clamping or pinching of the cervix. Particular implementations of a cervical stabilization device disclosed herein present light, incidental contact on the cervix, so as not to stimulate or damage the cervix. Specifically, implementations of cervical stabilization devices are not intended to engage the cervix to any functional degree. Implementations of the present device support the uterus, not the cervix, in order to resist the force upon the uterus and untimely elongation and effacement of the cervix which can lead to a premature birth.

One particular embodiment comprises a mechanical device, manufactured from a substance having at least a minimal degree of flexibility, such substance including, but not limited to, rubber, plastic, silicon polymer or other suitable material. The substance from which the device is manufactured may additionally comprise at least one embedded antibiotic accomplished by methods known in the art.

The device functions to provide a protective 'nest' to the cervix, surrounding at least a portion of the cervical tissue to prevent the pressure and weight of the developing fetus from extending the uterus deeper into the vagina, which can cause the cervix to efface and dilate. The nest serves to create a space for the cervix to reside, where it is not stimulated or in significant contact with the device. To stabilize the cervix without damaging tissue or compromising the natural "transformation" and biologies of the ectocervical tissues and mucous plug as the pregnancy advances, a particular implementation of the device comprises a uterine support shoulder configured to contact a portion of the vaginal wall proximate the entry of the cervix of the uterus into the vagina. The shoulder is coupled to a flexible disk-like annular portion that first engages the vaginal wall proximate the uterus then extends down to further dispose bearing forces upon the resilient tissues of the vaginal wall, and may finally to terminate opposing the tissues proximate the lower pelvic structure (generally, the sacrum, pubis, ischium, and pubic symphysis). In contrast, conventional devices, used as contraceptives or to retain prolapsed organs (such as the bladder, bowel, and uterus) and which are not used or intended for use during pregnancy or to prevent premature births, and those used to clamp the cervix without supporting the uterus, force contact on the cervix by primitive clamping or pinching the more delicate and reactive tissues of the cervix. The device can be produced in a wide range of geometries to assure the best fit and comfort of the patient, including, but not limited to, "spider-like" geometry or a full disc. Alternately, ultrasound or other imagining technologies may be utilized to map the patient's exact physical proportions and a fully custom-fit device can be quickly manufactured by a laboratory or other suitable manufacturer. Still alternatively, molding techniques may be used by inserting a moldable substance into the patient's vagina to map certain of the patient's exact physical proportions and a custom-fit device can then be manufactured.

As the need arises, the device can be easily removed and replaced in a simple procedure that may additionally be non-surgical and anesthetic-free, allowing the attending physician's close inspection of the uterus and surrounding tissues as the pregnancy progresses. As delivery time approaches, the device can be quickly and painlessly removed with little or no recovery time necessary, thereby allowing for the most natural delivery possible. Furthermore, as the patient's uterus expands, a cervical stabilization device of an accommodating size may be substituted for the previously used cervical stabilization device adapted to the growing fetus and resulting changes in uterus size and other physical factors to the patient's anatomy.

FIG. 1 illustrates a particular implementation of a cervical stabilization device. It should be understood that the embodiment in FIG. 1 is an embodiment illustrated outside of the human body and fully inflated. Cervical stabilization device 100 comprises a cervical nest 102 coupled to a vent tube 104. Vent tube 104 allows the natural discharges from the cervix to leave the body. Cervical nest 102 includes an enhanced contact portion surrounding a center, generally concave void portion, as seen more clearly in later illustrations. Surrounding vent tube 104 are inflatable bladder portions 106 and 108. Inflatable bladder portions 106 and 108 are inflated via inflation valves 112 and 114. Coupled to inflatable bladder portions 106 and 108 illustrated in FIG. 1, is an organ bridge 120. An organ bridge, or bridges, may be used to dispose of pressure that might otherwise compromise the function of surrounding organs such as the bladder and bowel.

Cervical nest 102 is designed to gently 'nest' the cervix while the uterine support shoulder portion (not shown) bears the weight and force of the developing fetus forcing down upon the uterus, disposing such forces to the more resilient vaginal wall tissues, thereby reducing the forces acting on a compromised cervix and the likelihood of preterm delivery.

Cervical nest 102 may be considered an optional component to the device 100, as the balloon portions may provide much of the same support. However, the cervical nest 102 allows for optimal cervical 'nesting' when carefully fitted to the patient by an appropriate healthcare professional, who may also be responsible for selecting the correct component sizes and the proper degree of inflation for each of the individual bladder portions.

Inflatable bladders portions 106 and 108 may be inflated by saline, air, inert gas, gels or any other suitable fluid(s) or materials, or otherwise inflated by decompressing a compressed material such as a foam, sponge or other bladder portion that has been compressed and can controllably be allowed to return toward its uncompressed state. The inflation may be precisely adjusted to provide a wide range of personal fit and adaptation to the patient's physical characteristics and needs. Inflation valves 112 and 114 may be designed to extend beyond the vaginal opening to maximize comfort, and allow the attending professional easy access for monitoring and adjusting the device. Alternatively, they may be terminated inside the vagina and accessed for adjustments as needed. In certain circumstances, termination inside the vagina may provide for a more comfortable device for mobile patients.

Inflatable bladder portions 106 and 108 may be made from a selection of suitable elastomeric materials, which may include but are not limited to rubber, plastic, or silicone-based materials capable of being formed into balloon portions and inflated or filled by any suitable methods to conform to a wide range of individual patient bio geometries. Alternatively, inflatable bladder portions 106 and 108 may be made from any suitable sponge-like or compressible material, including those materials that fall into the general range of 20 to 50 durometer on the Shore A Scale. It may be desirable for inflatable bladder portions 106 and 108 to be made from a transparent elastomer material, so that it is easier for the attending physician to remain visually apprised of the overall condition of the vaginal tissues. Furthermore, it may be desirable for the elastomer to be coated or embedded with antibiotics to protect from the risk of infection, and for the surface of inflatable bladder portions 106 and 108 to be textured to some extent to help secure its position within the vagina.

Figure 2:
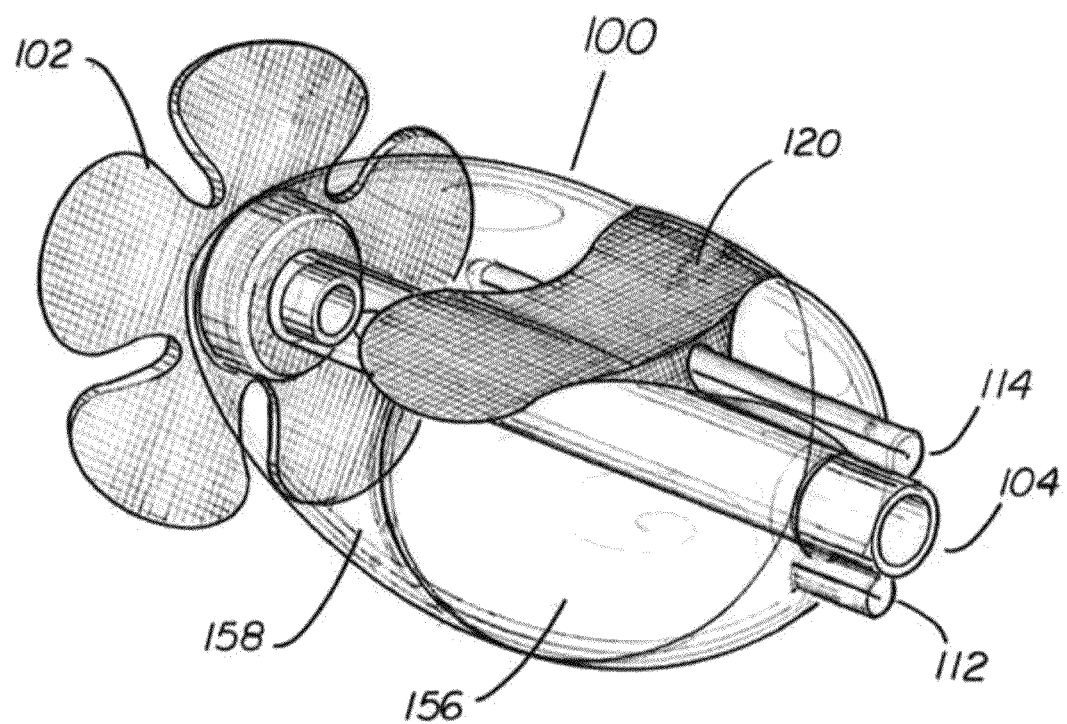
FIG. 2 is an isometric diagram illustrating another particular embodiment of a cervical stabilization device fully inflated and outside the vagina confines.

FIG. 2 illustrates an alternative configuration of cervical stabilization device 100. Cervical nest 102, vent tube 104, inflation valves 112 and 114, and organ bridge 120 are as described above with respect to FIG. 1. The key difference between FIG. 1 and FIG. 2 are the inflatable bladder portions. In FIG. 1, inflatable bladder portions 106 and 108 are longitudinally opposed about vent tube 104. In FIG. 2, inflatable bladder portions 156 and 158 are annular vessels opposed about the axis of vent tube 104.

Figure 3:
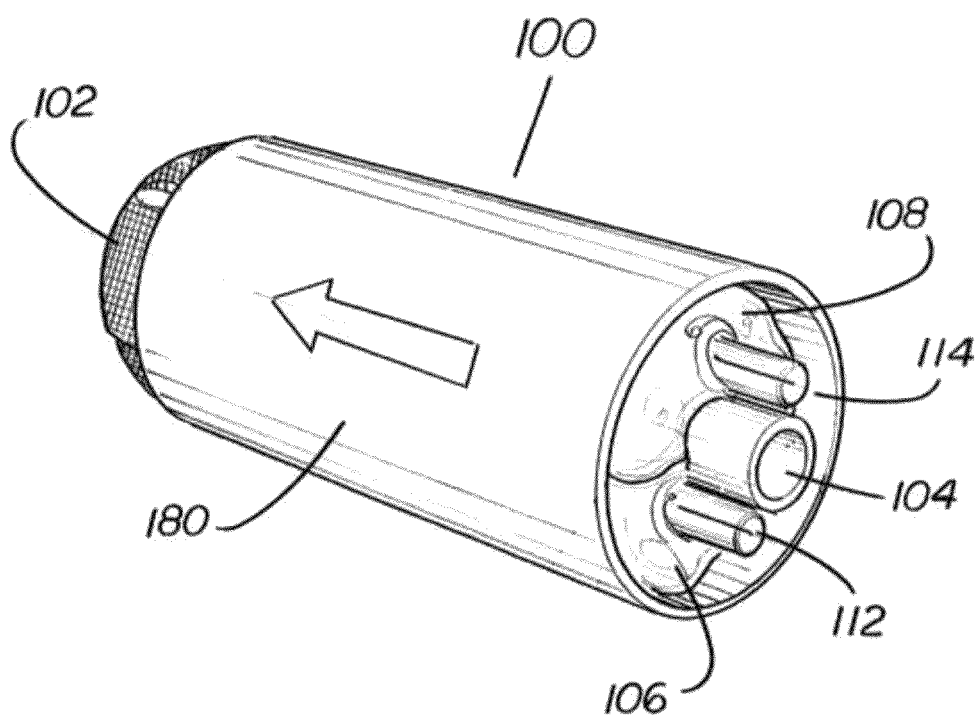
FIG. 3 illustrates a particular embodiment of a cervical stabilization device confined within an insertion sleeve.

While both FIG. 1 and FIG. 2 show the use of two inflatable bladder portions, it should be understood that a single inflatable bladder may also be used. In addition, three or more inflatable bladder portions may also be used FIG. 3 illustrates an embodiment of cervical stabilization device 100 in its deflated state. Cervical nest 102 has been folded and inflatable bladder portions 106 and 108 have been deflated such that cervical stabilization device 100 can be placed in insertion sleeve 180. Cervical stabilization device 100 is inserted into the patient in the direction of the arrow. Then the insertion sleeve 180 is removed and inflatable bladder portions 106 and 108 are inflated through the use of inflation valves 112 and 114.

Figure 6:
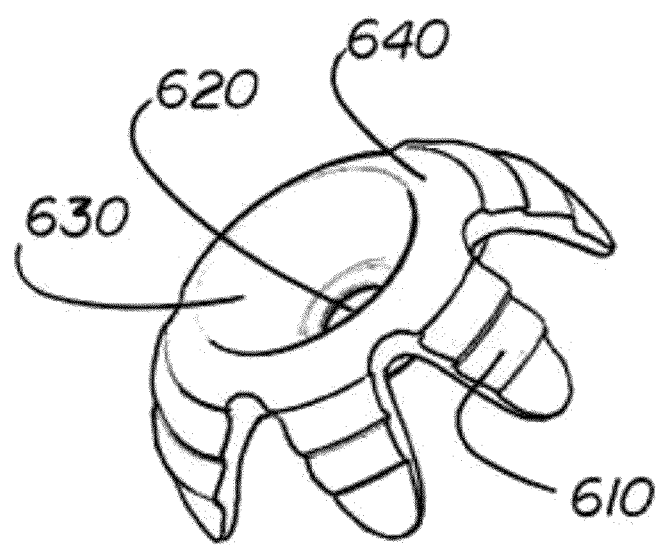
FIG. 6 is a detailed illustration of another particular embodiment of a cervical stabilization device.

FIG. 6 illustrates an isometric view of an embodiment that does not include inflatable bladder portions. The cervical stabilization device includes a seat portion 610, a vent 620, a central nesting area 630, and a uterine support shoulder 640. The central nesting area includes a generally concave void into which the cervix resides. The generally concave void is larger than the cervix, so that the nesting area surrounds and protects the cervix but does not engage, grip, squeeze, clamp or pinch the delicate and reactive cervical tissues as is common with conventional attempts to treat incontinent cervix. Vent 620 allows natural passage of discharges from the cervical canal to promote more normal biological function and to lessen the risk of infection or irritation of the cervix. Uterine support shoulder 640 occupies the space between the seat portion 610 and the nesting area 630. Uterine support shoulder 640 is coupled to and circumscribes nesting area 630. Seat portion 610 is depicted as having a plurality of portions extending from the uterine support shoulder 640. However, it should be understood that any number of seat portions, including a single circumferential seat portion, may be used in particular implementations. The operation of the seat portion 610, central nesting area 630, and uterine support shoulder 640 is similar to that described in the embodiment depicted in FIG. 4. Seat portion 610 is shown as having a plurality of ridges. However, it should be understood that seat portion 610 can also comprise a smooth surface, if it is desired to have less stress on the patient's vaginal walls.

Figure 7:
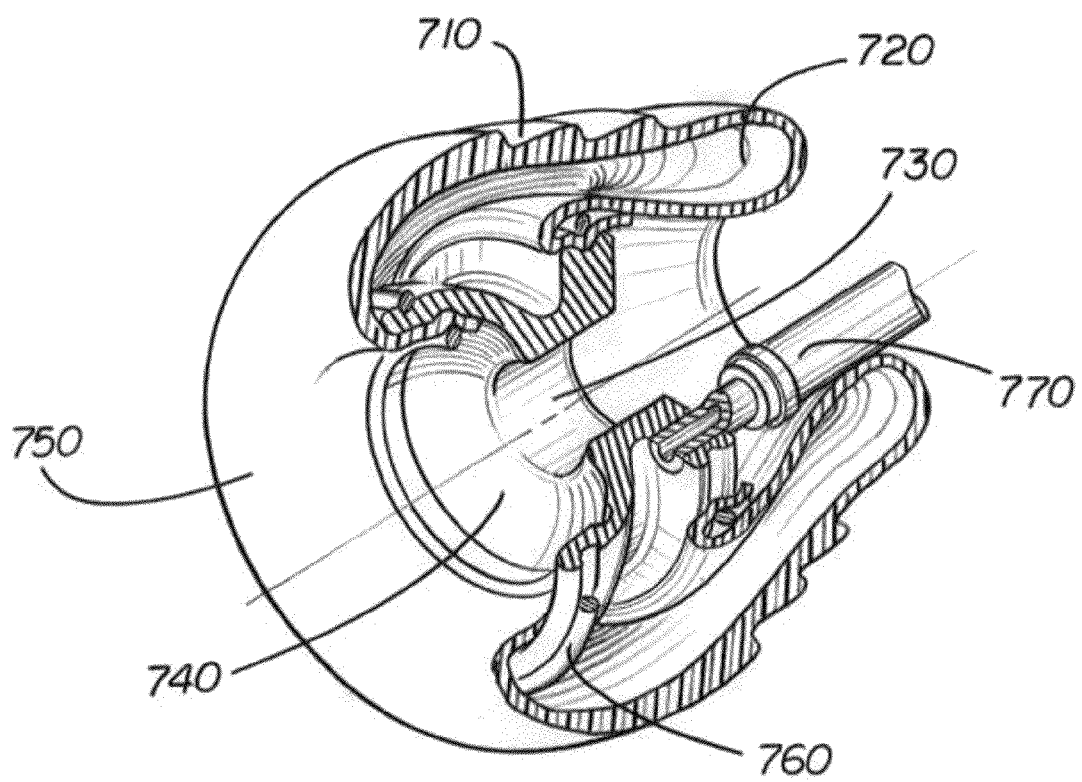
FIG. 7 is an isometric cross section illustration of another particular embodiment of a cervical stabilization device.

FIG. 7 illustrates an isometric cutaway view of another embodiment of the cervical stabilization device, including a cutaway view to show the interior of the design. The cervical stabilization device includes a seat portion 710, integral to inflatable bladder portion 720, a vent 730, a central nesting area 740, a uterine support shoulder 750, a radiologic placement ring 760 and an inflation valve assembly 770. The central nesting area 740 includes a generally concave void wherein the cervix resides and is protected. The generally concave void is larger than the cervix, so that the nesting area surrounds the cervix, but does not engage, grip, squeeze, clamp or pinch the delicate and reactive tissues of the cervix. Vent 730 allows natural passage of discharges from the cervical canal to promote more normal biological function and to lessen the risk of infection or irritation of the cervix. Uterine support shoulder 750 occupies the space between the seat portion 710 and the central nesting area 740. Bladder 720 may be inflated by saline, air, inert gas, gels or any other suitable fluid(s) or constructed to include flexible materials, or otherwise inflated by decompressing a compressed material such as a foam, sponge or other bladder portion that has been compressed and can controllably be allowed to return toward its uncompressed state. As bladder 720 is inflated, the interaction between the vaginal walls and seat portion 710 can be optimized to the patient's physical characteristics and needs. It should be understood that seat portion 710 can also be replaced by a smooth surface, if it is desired to place less stress on the patient's vaginal walls.

Figure 4:
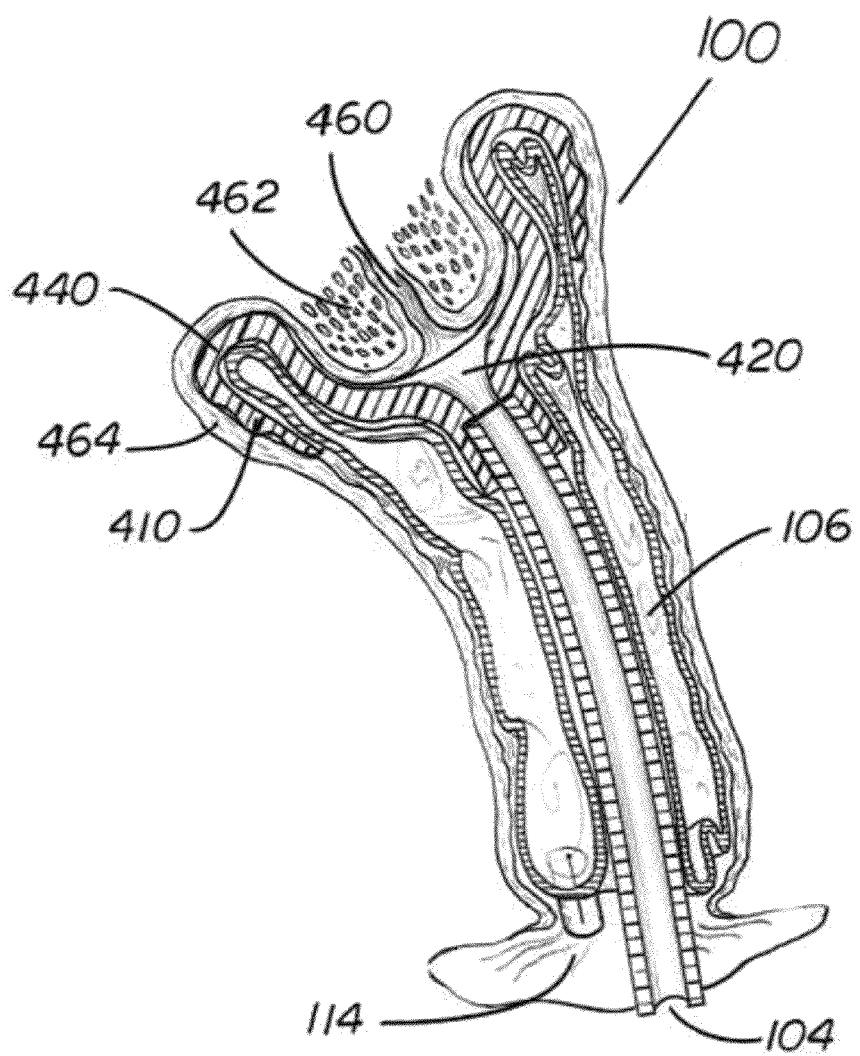
FIG. 4 is a cross section illustration of a particular embodiment of a cervical stabilization device positioned within the patient prior to inflation.

FIG. 4 is a cross sectional illustration of an embodiment of cervical stabilization device 100 that is fitted within a patient. A single inflatable bladder embodiment is shown, with inflatable bladder 106 surrounding vent tube 104. While shown in a deflated state, it should be understood that inflatable bladder 106 can be inflated through the use of inflation valve 114. The patient's anatomy as illustrated includes cervical canal 460, ectocervix 462, and vaginal wall 464.

In operation, as the ever increasing weight of the developing fetus produces force upon the uterus which then involves the ectocervical tissue and may cause untimely effacement of the compromised cervix leading to a premature birth, the cervical stabilization device 100 protects and stabilizes the cervix and ectocervix 462 by supporting the uterus via uterine support shoulder 440 and disposing the pressure to the more resilient vaginal wall 464, aided by the use of seat portions 410. Natural discharges from the cervix can travel through vent 420, which is coupled to vent tube 104.

Another particular implementation of the device comprises a structure providing support to the cervix without involving the vaginal wall. This implementation is particularly useful when a patient has sensitivities or conditions that might contraindicate involving the vaginal tissues (such as severe varicose veins or other medical conditions). One purpose for using this implementation includes providing the same gentle cradling of the cervix while limiting further settling and extension of the uterus into the vagina which is synchronous to the cervical effacement and dilation process.

Figure 5:
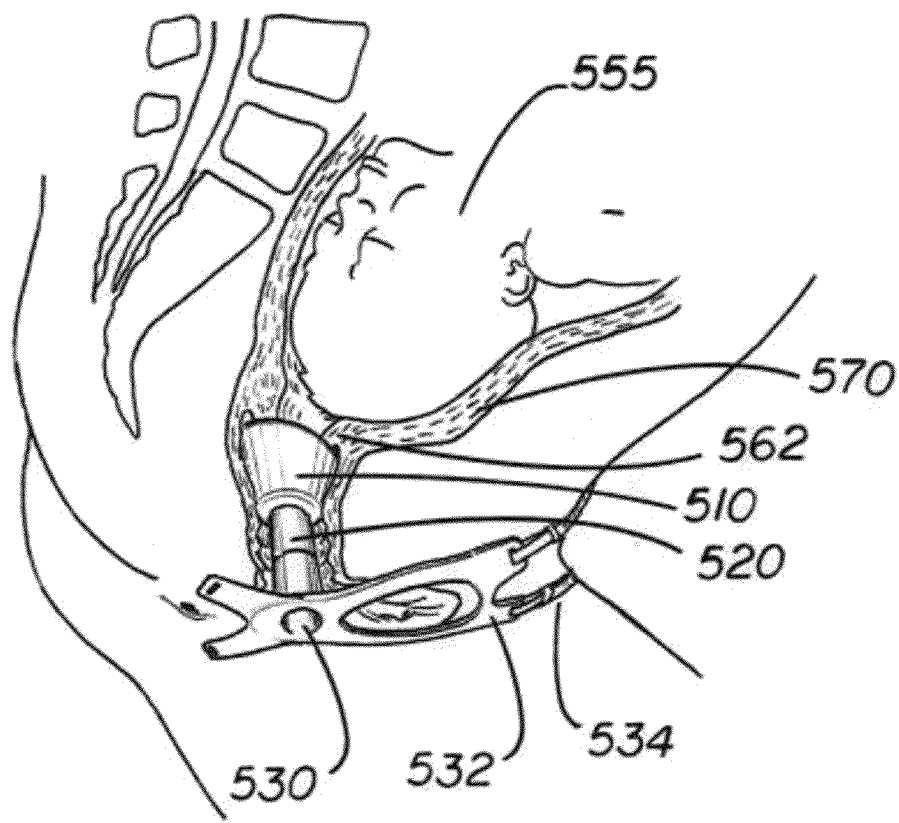
FIG. 5 is a cross section illustration of another particular embodiment of a cervical stabilization device inserted into a patient.

Referring now to FIG. 5, an adjustable nest 510 (including one or more accommodating features, as described above), is affixed to a support 520, which may be adjustable or selectable in length to accommodate various stages of pregnancy, and extends beyond the vaginal opening to a retaining portion 532 that is in turn supported by adjustable straps 534 which attach to a belt portion of the apparatus (not shown), or which may be held in position by other appropriate garment(s). Also illustrated is a vent 530, which serves the same purpose as the vents described above. Those portions in total provide a fully adjustable and reliable alternative to the more discreet, internal implementations previously described. Thus, the cervix 562 is supported to relieve pressure from developing fetus 555 within uterus 570. Individual components of a cervical stabilization device may be made from flexible polymers such as silicon-based rubber or gum, or other suitable materials. More rigid components of a cervical stabilization device, such as the support 520, may be made of less flexible polymers or other suitable materials. The flexible form-fitting components are intended to fit comfortably and comply with individual patient bio geometries.

The various embodiments of the cervical stabilization device operate in a similar manner. The cervical stabilization device is inserted into the vagina. The cervix is surrounded by a nesting area of the cervical stabilization device. The cervical stabilization device is positioned such that the cervix is not engaged by the nesting area, so to lessen the amount of stimulation/disruption of the cervix. Discharges emanating from the cervical canal are drained through a vent in the nesting area. The uterine support shoulder of the cervical support device, which surrounds the nesting area, supports weight bearing down upon the uterus. The uterine support shoulder is coupled to a seat portion of the cervical stabilization device. The seat portion engages the vaginal wall, thus helping the uterine support shoulder to support the uterus. In an embodiment with an inflatable bladder, the bladder is generally beneath the seat portion and serves to help engage the seat portion with the vaginal wall. The bladder may also function such as to reduce the strain upon the cervix by resisting the downward force upon the uterus by disposing such bearing forces upon the resilient tissues of the vaginal wall (which may be aided by the seat portion) and by expanding to fill the vagina to such a degree as to extend the bladder to terminate opposing the tissues proximate the lower pelvic structure to resist displacement and expulsion of device. The supporting of the uterus and protection/stabilization of the cervix being continuous for an extended period of time, such as the days, week or weeks that typically exists between office visits rather than merely the time during a particular office visit, or for so long as may be prescribed by the attending physician throughout specific stages of a troubled pregnancy.

It is important to note that all of the embodiments discussed above, as well as other implementations not specifically discussed in this description but which become apparent from this description when combined with the knowledge of one of ordinary skill in the art, may be customized to improve the fit of the device and comfort for a particular patient. The use of the device may also lead to the need for improved insertion, positioning, and extraction instruments to facilitate the utilization of the device and further enhance patient comfort.

The implementations listed here, and many others, will become readily apparent from this disclosure. From this, those of ordinary skill in the art will readily understand the versatility with which this disclosure may be applied. Implementations of a cervical stabilization device may be constructed of a wide variety of materials, including as described above. Those of ordinary skill in the art will readily be able to select appropriate materials and manufacture these products from the disclosures provided herein.

Some components defining a cervical stabilization device may be manufactured simultaneously and integrally joined with one another, while other components may be purchased pre-manufactured or manufactured separately and then assembled with the integral components. Various implementations may be manufactured using conventional procedures as added to and improved upon through the principles described here.

Accordingly, manufacture of these components separately or simultaneously may involve vacuum forming, injection molding, blow molding, milling, drilling, reaming, stamping, pressing, cutting and/or the like. Components manufactured separately may then be coupled or removably coupled with the other integral components in any manner, such as with an adhesive, a weld joint, a fastener any combination thereof, and/or the like for example, depending on, among other considerations, the particular material forming the components. Particular manufacturing techniques and materials are used in the medical industry for safety purposes and have been approved by the relevant authorities. It is anticipated that these approved materials and manufacturing techniques known in the art will be used in manufacturing the various implementations of cervical stabilization devices described in and apparent from this disclosure.

It will be understood that implementations are not limited to the specific components disclosed herein, as virtually any components consistent with the intended operation of a method and/or system implementation for a cervical stabilization device may be utilized. Accordingly, for example, although particular component examples may be disclosed, such components may comprise any shape, size, style, type, model, version, class, grade, measurement, concentration, material, weight, quantity, and/or the like consistent with the intended operation of a method and/or system implementation for a cervical stabilization device may be used.

In places where the description above refers to particular implementations of a cervical stabilization device, it should be readily apparent that a number of modifications may be made without departing from the spirit thereof and that these implementations may be applied to other cervical stabilization devices. The presently disclosed implementations are, therefore, to be considered in all respects as illustrative and not restrictive.

I claim:

1. A device for stabilizing a cervix of a uterus during pregnancy comprising:
    a uterine support shoulder comprising an upper shoulder portion configured to contact a portion of a vaginal wall of a vagina proximate entry of the cervix of the uterus into the vagina, the uterus carrying a fetus, the uterine support shoulder coupled to and at least partially circumscribing a nesting area configured to receive a cervix extending from the uterus, the cervix comprising a cervical canal and an outer surface extending from the vaginal wall into the vagina, the nesting area comprising a void larger than an outer dimension of the cervix so that the nesting area surrounds but does not engage the outer surface of the cervix between the entry of the cervix into the vagina and an opening of the cervical canal, the nesting area further comprising a vent extending through the nesting area; and
    at least one seat portion extending anatomically outward and downward from the uterine support shoulder, the at least one seat portion configured to engage walls of the vagina surrounding the cervix and resist movement of the uterine support shoulder away from the portion of the vaginal wall proximate the entry of the cervix of the uterus into the vagina.

2. The device of claim 1, further comprising at least one inflatable bladder positioned around at least a portion of the nesting area and between the nesting area and the at least one seat portion, wherein inflating the bladder portion causes the at least one seat portion to extend away from the nesting area and press the at least one seat portion against the vaginal wall.

3. The device of claim 2, further comprising at least one vent tube coupled to the nesting area at the at least one vent in communication with the concave void.

4. The device of claim 2, wherein the at least one inflatable bladder portion comprises at least two bladder portions adjacent to each other, each of a first and a second of the at least two bladder portions extending from the nesting area along a vent tube coupled to the vent of the nesting area.

5. The device of claim 2, wherein the at least one inflatable bladder extends from the nesting area along a vent tube coupled to the vent of the nesting area, the device further comprising at least another inflatable bladder that extends from the first inflatable bladder along the vent tube away from the first inflatable bladder.

6. The device of claim 1, wherein the at least one seat portion comprises a plurality of separate seat portions, each extending in a different radial direction from the uterine support shoulder and each comprising the plurality of ridges.

7. The device of claim 1, wherein the at least one seat portion is in communication with an inflatable bladder portion, wherein inflating the bladder portion causes the at least one seat portion to expand and press the at least one seat portion against the vaginal wall.

8. The device of claim 1, further comprising at least one inflatable bladder positioned around at least a portion of the nesting area, wherein the inflatable bladder portion is configured such that inflating the bladder portion causes the at least one inflatable bladder portion to extend and engage the vaginal wall proximate a lower pelvic structure adjacent the vagina.

9. The device of claim 1, wherein the at least one seat portion is integral with an inflatable bladder portion, wherein inflating the bladder portion causes the at least one seat portion to expand and press the at least one seat portion against the vaginal wall.

10. A method of stabilizing a cervix during pregnancy, the method comprising:
    at least partially surrounding a cervix of a uterus carrying a fetus with a nesting area of a cervical stabilization device without engaging the cervix;
    permitting the cervix to drain fluid from the nesting area through a vent in the nesting area;
    supporting a portion of a vaginal wall of a vagina proximate entry of the cervix of the uterus into the vagina with a uterine support shoulder of the cervical stabilization device, the uterine support shoulder at least partially surrounding the nesting area; and
    maintaining the support of the portion of the vaginal wall proximate entry of the cervix into the vagina through engaging vaginal walls surrounding the cervix with at least one seat portion coupled to and extending anatomically outward and downward from the uterine support shoulder.

11. The method of claim 10, wherein maintaining the support of the portion of the vaginal wall proximate entry of the cervix through engaging vaginal walls surrounding the cervix comprises engaging the vaginal walls for an extended period of time without removing the cervical stabilization device.

12. The method of claim 11, wherein maintaining the support of the portion of the vaginal wall proximate the entry of the cervix of the uterus into the vagina for an extended period of time comprises maintaining the support for at least a week without removing the cervical stabilization device.

13. The method of claim 11, wherein maintaining the support of the portion of the vaginal wall proximate the entry of the cervix of the uterus into the vagina for an extended period of time comprises maintaining the support for at least a month without removing the cervical stabilization device.

14. The method of claim 10, further comprising inflating at least one bladder portion positioned beneath the at least one seat portion such that when the at least one bladder is inflated it enlarges and pushes the at least one seat portion toward the vaginal walls surrounding the cervix.

15. The method of claim 14, further comprising inflating the at least one bladder portion such that an anatomically lower portion of the at least one bladder portion contacts anatomically lower vaginal tissues proximate an anatomically lower pelvic structure adjacent the vagina.

16. The method of claim 14, wherein the at least one bladder is positioned beneath the at least one seat portion on a first side of the nesting area, the method further comprising inflating at least a second bladder adjacent to the at least one bladder, the at least a second bladder positioned beneath the at least one seat portion on a second side of the nesting area.

17. The method of claim 14, further comprising inflating at least a second bladder adjacent to the at least one bladder, the at least a second bladder being positioned along a vent tube coupled to the vent in the nesting area.

18. The method of claim 10, further comprising inserting the cervical stabilization device into the vagina prior to supporting a portion of the vaginal wall proximate the entry of the cervix of the uterus into the vagina.

19. The method of claim 10, further comprising permitting the cervix to further drain the fluid through a vent tube coupled to the vent in the nesting area.

20. The method of claim 10, wherein maintaining the support of the portion of the vaginal wall proximate the entry of the cervix through engaging vaginal walls surrounding the cervix comprises engaging the vaginal walls with a plurality of separately moveable seat portions each extending in a different radial direction from the uterine support and each contacting a different portion of the vaginal walls surrounding the cervix.

21. The method of claim 10, wherein maintaining the support of the portion of the vaginal wall proximate the entry of the cervix of the uterus into the vagina comprises inflating at least one bladder portion incorporated within the at least one seat portion.

* * * * *